US008321153B2

(12) United States Patent
Park et al.

(10) Patent No.: US 8,321,153 B2
(45) Date of Patent: Nov. 27, 2012

(54) METHOD FOR DETERMINING ISOTOPIC CLUSTERS AND MONOISOTOPIC MASSES OF POLYPEPTIDES ON MASS SPECTRA OF COMPLEX POLYPEPTIDE MIXTURES AND COMPUTER-READABLE MEDIUM THEREOF

(75) Inventors: Kun Soo Park, Seoul (KR); Joo Young Yoon, Seoul (KR); Sun Ho Lee, Seoul (KR); Eun Ok Paek, Seoul (KR); Hee Jin Park, Seoul (KR); Sang Won Lee, Seoul (KR)

(73) Assignees: SNU R & DB Foundation, Seoul (KR); University of Seoul Foundation of Industry Academic Cooperation, Seoul (KR)

( * ) Notice: Subject to any disclaimer, the term of this patent is extended or adjusted under 35 U.S.C. 154(b) by 439 days.

(21) Appl. No.: 12/526,607

(22) PCT Filed: Dec. 28, 2007

(86) PCT No.: PCT/KR2007/006937

§ 371 (c)(1), (2), (4) Date: Dec. 14, 2009

(87) PCT Pub. No.: WO2008/096962

PCT Pub. Date: Aug. 14, 2008

(65) Prior Publication Data

US 2010/0114498 A1 May 6, 2010

(30) Foreign Application Priority Data

Feb. 8, 2007 (KR) ........................ 10-2007-0013405

(51) Int. Cl.
*G01N 33/48* (2006.01)
*G01N 33/50* (2006.01)
*G01N 31/00* (2006.01)
*C12Q 1/00* (2006.01)

(52) U.S. Cl. ................ 702/23; 702/19; 702/22; 702/27; 435/4

(58) Field of Classification Search ........................ None
See application file for complete search history.

(56) References Cited

U.S. PATENT DOCUMENTS

2003/0109990 A1 6/2003 Axelsson

FOREIGN PATENT DOCUMENTS

WO WO 01/67485 A1 9/2001

OTHER PUBLICATIONS

David M. Horn, et al.; Automated Reduction and Interpretation of High Resolution Electrospray Mass Spectra of Large Molecules; American Society for Mass Spectrometry 2000, 11, 320-332.

(Continued)

*Primary Examiner* — Russell S Negin

(57) ABSTRACT

Disclosed herein is a method of finding an isotopic cluster in a polypeptide and determining the monoisotopic mass of the cluster. The method comprises an algorithm for finding an isotopic cluster based on a probabilistic model, defined by each of peaks in the isotopic cluster, and determining the monoisotopic mass of the isotopic cluster. The probabilistic model of the isotopic cluster includes characteristic functions for mass, that is, a function of the ratio of two peak intensities, and a function of the product of two ratios obtained from three peaks. These characteristic functions for mass define the shape of peaks acceptable in an actual isotopic cluster for the mass of any isotopic cluster. The algorithm of finding the isotopic cluster based on the functions uses the characteristics to score the degree of the approximation of any isotopic cluster to the spectral shape of a theoretical cluster.

17 Claims, 6 Drawing Sheets

OTHER PUBLICATIONS

Michael W. Senko, et al.; Determination of Monoisotopic Masses and Ion Populations for Large Biomolecules from Resolved Isotopic Distributions; American Society for Mass Spectrometry 1995, 6, 229-233.

Kunsoo Park et al., "Isotopic Peak Intensity Ratio Based Algorithm for Determination of Isotopic Clusters and Monoisotopic Masses of Polypeptides from High-Resolution Mass Spectrometric Data", Analytical Chemistry, vol. 80, No. 19, Oct. 1, 2008, pp. 7294-7303.

Parminder Kaur et al., "Algorithms for Automatic Interpretation of High Resolution Mass Spectra", American Society for Mass Spectrometry, 2006, pp. 459-468, vol. 17, Elsevier Inc.

Dirk Valkenborg et al., "A Model-Based Method for the Prediction of the Isotopic Distribution of Peptides", American Society for Mass Spectrometry, 2008, pp. 703-712, vol. 19, Elsevier Inc.

Anna Gambin et al., "Automated reduction and interpretation of multidimensional mass spectra for analysis of complex peptide mixtures", International Journal of Mass Spectrometry, pp. 20-30, vol. 260, Elsevier B.V., Published online on Aug. 4, 2006.

METHOD FOR DETERMINING ISOTOPIC CLUSTERS AND MONOISOTOPIC MASSES OF POLYPEPTIDES ON MASS SPECTRA OF COMPLEX POLYPEPTIDE MIXTURES AND COMPUTER-READABLE MEDIUM THEREOF

TECHNICAL FIELD

The present invention relates to a method of finding isotopic clusters for each polypeptide from the mass spectrum of a polypeptide mixture and determining the monoisotopic mass of the monoisotope, and to a recording medium which enables the method to be programmed and executed by a computer.

BACKGROUND ART

The mass spectrometry of a polypeptide mixture is a technique that is applied in protein studies, and the interpretation of mass spectra makes it possible to identify or quantify proteins in the mixture. Disclosed herein is a method of determining the mass of polypeptides using mass spectra, which is the most fundamental step among the steps of interpreting mass spectra, and will become the basis of advanced spectral interpretation in the future.

Mass spectral data are stored as a list of peaks. Each peak is defined as the mass-to-charge ratio (m/z) and the intensity of polypeptides in a mixture. The mixture of polypeptides becomes positively charged ions combined with protons $H^+$ through a mass spectrometer, and the polypeptide ions are detected as the mass-to-charge ratio (m/z) and intensity thereof instead of the direct mass in the mass spectra.

In initial spectral data obtained using the mass spectrometer, the mass-to-charge ratio of peaks can be determined either through continuous waveform data, which cannot define the definite locations of peaks, that is, mass-to-charge rations, or through a suitable peak-picking procedure. The method provided herein is based on mass spectral data subjected to such a peak-picking procedure.

The mass of a polypeptide is defined, for example, as the sum of masses of carbon (C), hydrogen (H), nitrogen (N), oxygen (O) and sulfur (S) atoms in the relevant peptide, and uses monoisotopic mass as a representative value. As used herein, the term “monoisotopic mass” refers to the sum of masses of atoms, on the assumption that the atoms of a polypeptide are all present in the lightest isotopic forms thereof. All elements present in nature have isotopes. For example, for the carbon atom, $^{12}C$ and $^{13}C$ isotopes exist, and $^{13}C$ is present at a rate of 1%. Thus, for a given polypeptide, if any atoms correspond to heavy isotopes, several peaks having different mass values can be detected in the spectrum. For this reason, monoisotopic mass is used as a value representative of a polypeptide. However, it is a difficult problem to find a peak corresponding to monoisotopic mass directly in an actual spectrum, because complicated and overlapping peaks can appear in the spectrum due to the difference in isotopic mass between several polypeptides, and the larger the mass of a polypeptide, the lower the likelihood that the atoms of the polypeptide will all consist of the lightest isotopes.

If polypeptides having the same elementary composition show different peaks in the spectra due only to the difference in monoisotopic mass therebetween, the group of such peaks is defined as an isotopic cluster. The peaks of this isotopic cluster continuously appear with a mass difference of 1 Da (Dalton), and because of the charges (z) of polypeptide ions, the peak interval of mass-to-charge ratio (m/z) in the actual spectrum is a constant interval of 1/z. If mass spectral data are interpreted to find an isotopic cluster consisting of the same polypeptide ions, the charge and monoisotopic mass of the isotopic cluster can be determined.

Prior typical programs for finding this isotopic cluster and determining the monoisotopic mass of the cluster include ICR2LS. ICR2LS employs the following method, known as the THRASH algorithm. This method comprises selecting peaks, which can become candidates of the isotopic cluster, from a spectrum, and comparing the selected peaks with the peak shape of the isotopic cluster based on the averagine composition to determine the isotopic cluster.

The concrete procedure of the THRASH algorithm is as follows. First, about 1 m/z is taken in a suitable region in a spectrum, and the peak having the highest intensity in the relevant region is selected. Peaks having a constant distance around the relevant peak are selected to determine a candidate isotopic cluster, and the charge of the candidate isotopic cluster is calculated to obtain an approximate mass close to the monoisotopic mass. From the approximate mass, the peak intensities of the isotopic cluster based on the pre-calculated averagine composition can be obtained. The peak shape of the theoretical isotopic cluster is compared with the peak shape of the candidate isotope cluster to calculate the error in the peak intensities, and if the error is sufficiently small, the candidate isotope cluster is judged to be the isotopic cluster. If the candidate isotope cluster cannot be judged to be the isotopic cluster because the error is great, the charge is changed to determine a candidate isotopic cluster again, and the above-described procedures are repeated.

In the case of THRASH, if the elementary composition of a polypeptide, measured through mass spectrometry, deviates from the averagine composition, a great error in the peak intensity can occur, because the peak shape of the isotopic cluster does not coincide well with the pre-calculated peak shape of the isotopic cluster. The peak location and intensity distribution of the isotopic cluster based on the averagine composition are determined only by mass, but the peak distribution based on the actual isotopes is determined by the number of elements of the polypeptide. Herein, the actual events can differ greatly from the theoretical events due to the incompleteness of procedures for processing ionic signals (e.g., a procedure for digitizing superimposed current as a function of time, and signal amplification/modification procedures) and the non-probabilistic isotopic distribution, resulting from a decrease in actual ion number. In this case, THRASH cannot accurately determine the peak locations of monoisotopes. Another known problem is that the processing speed in a procedure of comparing the peak shapes of the isotopic clusters becomes significantly slow.

DISCLOSURE

Technical Problem

The present invention has been made in order to solve the above-described problems occurring in the prior art, and it is an object of the present invention to overcome the shortcomings of THRASH so as to perform the determination of a monoisotopic cluster and the determination of monoisotopic mass in a more precise and rapid manner. For this purpose, the present invention provides a method for determining monoisotopic mass and a recording medium for carrying out the method, which can: (1) determine the locations of actual monoisotopic peaks without errors, even when the elementary composition of polypeptides deviates from the averagine composition; (2) precisely determine each of isotopic clusters, even when the peaks of each of the isotopic clusters overlap in a complicated way, because several polypeptides appear in mass spectral data; (3) increase processing speed in a procedure of comparing the peak shapes of isotopic clusters; and (4) increase the accuracy of a method of calculating monoisotopic mass from isotopic clusters.

Technical Solution

The present invention encompasses a probabilistic model of intensity of each of peaks in isotopic clusters, and an algorithm for finding isotopic clusters based on the model and determining accurate masses. The probabilistic models of isotopic clusters comprise characteristic functions of mass, including a function of the ratio of two peak intensities, and a function of the product of two ratios obtained from three peaks. In order to determine the characteristic functions of isotopic clusters, the intensity of each peak can be expressed as a function of the number of elements of the relevant polypeptide, but probabilistic models are obtained by approximating the ratio of peak intensities and the product of ratios as a function of mass, because the elementary composition of the polypeptide cannot be directly determined. These characteristic functions of mass are defined as the maximum, minimum and average of the ratio and the product of ratios possible to the mass of an actual isotopic cluster to the mass of any isotopic cluster.

In the present invention, the algorithm of finding isotopic clusters on the basis of the above-described probabilistic model comprises scoring the similarity of any isotopic cluster to the shape of an actual isotopic cluster on the basis of the characteristic functions. In the algorithm, three peaks, which can indicate the same isotopic cluster, are first found at a distance of 1 Da, and then the scores thereof are calculated in consideration of, whether the ratio and the product of ratios of peak intensities falls in the range of the maximum and minimum values of the predetermined characteristic functions, and the similarity to the average value. As the initial isotopic clusters, each having three peaks, are found, expandable peaks are additionally found at a distance of 1 Da, the scores thereof are calculated in the same manner, and the scores of isotopic clusters are renewed. Also, in the case of isotopic clusters in which three peaks cannot be found at the initial stage and which consist of only two peaks, only the ratio of the peaks is applied to calculate the scores. Through the above-described procedures, each isotopic cluster can be determined. Finally, overlapping isotopic clusters are removed, such that each peak belongs only to the respective isotopic clusters, and the monoisotopic mass of each isotopic cluster is determined.

The methods of determining the monoisotopic mass of isotopic clusters according to the present invention, which has been made in order to solve the problems occurring in the prior art, are summarized as follows.

According to one aspect of the present invention, the method of determining the probabilistic model of an isotopic cluster for determining the mass of the isotopic cluster comprises the steps of: approximating the intensity ($I_k$) of each peak in the isotopic cluster, the ratio ($I_{k+1}/I_k$) of two peak intensities, and the product $$\left(\frac{I_{k-1}I_{k+1}}{I_k^2}\right)$$

of two ratios obtained from three peaks, to a probabilistic equation; and using said probabilistic equation to determine the maximum, minimum and average functions ($R_{max}(k, M)$, $R_{min}(k, M)$ and $R_{avg}(k, M)$) of the $k^{th}$ ratio of a polypeptide having a mass of M, and the maximum, minimum and average functions ($RP_{min}(k, M)$, $RP_{max}(k, M)$ and $RP_{avg}(k, M)$) of the product of the $k^{th}$ ratio of the polypeptide having a mass of M.

According to another aspect of the present invention, the method of determining monoisotopic mass by finding an isotopic cluster from a mass spectrum and determining monoisotopic mass, the method comprising the steps of: selecting peaks in the order of mass-to-charge ratio (m/z) in a mass spectrum, and then finding isotopic clusters, having a charge state of 1-10 z, starting from the peaks; dividing the found isotopic clusters into a case consisting of more than 3 peaks and a case consisting of two peaks, and calculating the score of each of the cases; removing any one of two isotopic clusters having an overlapping peak among the isotopic clusters having calculated scores higher than a threshold score; and calculating the mass of each of the isotopic clusters having calculated scores higher than the threshold score.

The method of determining monoisotopic mass according to still another aspect of the present invention comprises the steps of: selecting peaks in the order of mass-to-charge ratio (m/z) in a mass spectrum, and finding isotopic clusters including peaks in a region spaced by a given mass starting from the selected peaks for a given range of charge; calculating the similarity of each of the found isotopic clusters to a theoretical isotopic cluster using characteristic functions for the ratio of two peaks or the product for two ratios obtained from three peaks, and calculating the monoisotopic mass of the isotopic clusters having calculated scores higher than a threshold score, wherein, in the step of calculating the score, the score for each of the isotopic clusters is calculated in consideration of whether a given ratio and a ratio product, based on each of the intensities of the peaks, fall within the previously defined maximum and minimum values based on the characteristic functions, and if isotopic clusters including the same peak exist among the isotopic clusters having scores higher than a threshold score, only an isotopic cluster having a higher priority is selected.

According to yet another aspect, in the inventive method of finding the isotopic cluster from the mass spectrum and determining the monoisotopic mass of the isotopic cluster, a probabilistic model, in which probability equations for the ratio of two peak intensities and the product of two ratios obtained from three peaks are expressed as characteristic functions associated with mass, is used to score the similarity of the found isotopic cluster to a theoretical isotopic cluster and calculate the monoisotopic mass of each of the selected isotopic clusters.

Advantageous Effects

In the inventive method of finding an isotopic cluster and determining the monoisotopic mass of the isotopic cluster, the problems of THRASH, which is a typical method that is most frequently used in the prior process of processing a large amount of high-resolution mass spectrometry data, can be solved.

Also, in the inventive method of finding an isotopic cluster and determining the monoisotopic mass of the isotopic cluster, the locations of monoisotopic peaks can be accurately determined even when the elementary composition of a polypeptide deviates from the averagine composition. Also, each of isotopic clusters can be accurately determined, even when various polypeptides appear in mass spectral data, such that the peaks of the isotopic clusters overlap in a complicated manner.

In addition, in the inventive method of finding an isotopic cluster and determining the monoisotopic mass of the isotopic cluster, a process of comparing the spectral shape of the isotopic clusters is not carried out, and thus problems associated with processing speed, highlighted as the shortcomings of THRASH, can be solved, and the accuracy of calculation of monoisotopic mass can be increased, so that the theoretical mass is closely approached.

BEST MODE

Figure 1:
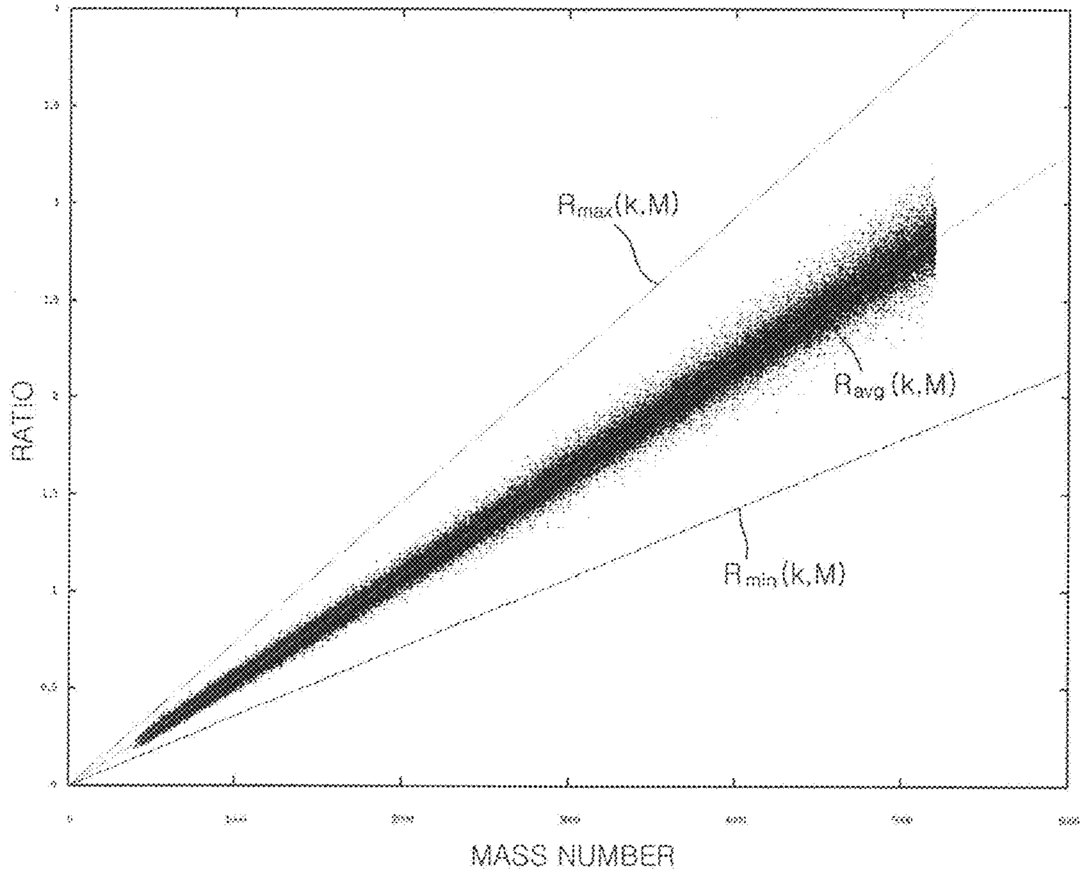
FIG. 1 shows an example of the maximum, minimum and average functions of peak intensity ratio for mass according to an embodiment of the present invention.

In order to fully understand the present invention, the operational advantages of the present invention and the objects accomplished by practicing the present invention, reference should be made to the attached drawings and the contents of the drawings, illustrating preferred embodiments of the present invention.

Hereinafter, the present invention will be described in detail with reference to the attached drawings.

Probabilistic Model for Peak Intensity in Isotopic Cluster

First, a probabilistic model for peak intensity in an isotopic cluster will be described. The probabilistic model on which the algorithm of the present invention is based is obtained through the following three steps.

In the first step, peak intensities $I_1, I_2, \ldots, I_k$ are represented as shown in Equation 1 according to the number of atoms in a polypeptide and the probability of existence of an isotope of each atom. As shown in Equation 1, the numbers of the carbon (C), hydrogen (H), nitrogen (N), oxygen (O) and sulfur (S) atoms of a polypeptide are assumed to be $n_C$, $n_H$, $n_N$, $n_O$ and $n_S$, respectively, and the probability of the existence of each isotope is expressed as P(X, n). P(X, n) means the probability of the existence of an isotope, having a mass of +n, among isotopes X. The first peak intensity $I_1$ becomes the probability that all of the isotopes will consist of monoisotopes; the second peak intensity $I_2$, the probability that the peptide will contain one isotope having a mass of +1; and the third peak intensity $I_3$, the probability that the peptide will contain two isotopes having a mass of +1, or one isotope having a mass of +2. Likewise, as shown in Equation 1, each of $I_4$ and $I_5$ means the probabilities that the peptide will contain one of isotopes having masses of +3 and +4, respectively, and the remaining $k^{th}$ peak intensities $I_k$ can be indicated by probability equations similar thereto.

$$I_1 = P(C,0)^{n_C} P(H,0)^{n_H} P(N,0)^{n_N} P(O,0)^{n_O} P(S,0)^{n_S} \quad \text{[Equation 1]}$$

$$I_2 = I_1 Y,\ Y = \frac{n_C P(C,1)}{P(C,0)} + \frac{n_H P(H,1)}{P(H,0)} + \frac{n_N P(N,1)}{P(N,0)} + \frac{n_O P(O,1)}{P(O,0)} + \frac{n_S P(S,1)}{P(S,0)}$$

$$I_3 = 1_1\left(\frac{Y^2}{2} + Z\right)$$

$$Z = \frac{n_O P(O,2)}{P(O,0)} + \frac{n_S P(S,2)}{P(S,0)}$$

$$I_4 = I_1\left(\frac{Y^3}{3!} + YZ\right)$$

$$I_5 = I_1\left(\frac{Y^4}{4!} + \frac{Y^2 Z}{2!} + \frac{Z^2}{2!} + W\right)$$

$$W = \frac{n_S P(S,4)}{P(S,0)}$$

In the second step, characteristic functions of the ratio of peak intensities and the product of the ratios, belonging to the probabilistic model, are expressed as a function of mass M. The number of atoms contained in the peak intensity equation can be approximately replaced with a proportional equation for M, and thus the ratios of peak intensities, $$\frac{I_2}{I_1}, \frac{I_3}{I_2} \cdots, \frac{I_{k+1}}{I_k},$$

and the products of the ratios, $$\frac{I_1 I_3}{I_2^2}, \frac{I_2 I_4}{I_3^2} \cdots, \frac{I_{k-1} I_{k+1}}{I_k^2},$$

can be approximated as a function of mass M. For this purpose, the ratio of peak intensities is calculated as shown in Equation 2. Herein, Y and Z are terms including the number $n_X$ of atoms X and the probability P(X, n) of the existence of isotopes, shown in the above-determined $I_k$ probability equation. The products of ratios of the remaining $k^{th}$ peak intensities, $$\frac{I_{k+1}}{I_k},$$

can be calculated in the same manner.

$$\frac{I_2}{I_1} = Y \quad \text{[Equation 2]}$$

$$\frac{I_3}{I_2} = \frac{Y}{2} + \frac{Z}{Y}$$

$$\frac{I_4}{I_3} = \frac{Y^3/3 + 2YZ}{Y^2 + 2Z}$$

Also, the products of the ratios of peak intensities are as shown in Equation 3. The products of the ratios of the remaining $k^{th}$ peaks, $$\frac{I_{k-1}I_{k+1}}{I_k^2},$$

can be calculated in the same manner.

[Equation 3]

$$\frac{I_1I_3}{I_2^2} = \frac{1}{2} + \frac{Z}{Y^2}$$

$$\frac{I_2I_4}{I_3^2} = \frac{2}{3} + \frac{4Z(Y^2-2Z)}{3(Y^2+2Z)^2}$$

$$\frac{I_3I_5}{I_4^2} = \frac{3}{4} + \frac{7Y^4Z+72Y^2W+72Z^3+144ZW}{4Y^6+48Y^4Z+144Y^2Z^2}$$

Then, the variables $n_X$, indicating the number of atoms in the polypeptide in the above characteristic equation, are substituted with a proportional expression of mass. If the polypeptide is in accordance with the averagine composition, the number of atoms is known to be calculated according to the equation $$n_X = \frac{X_{avg}}{M_{avg}}M$$

($M_{avg}$: averagine mass, $X_{avg}$: number of atoms in the averagine, and M: mass of isotopic cluster). Thus, the peak intensities can be indicated by an equation associated with the mass M of an isotopic cluster, as shown in Equation 4. The ratios of the remaining $k^{th}$ peak intensities, $$\frac{I_{k+1}}{I_k},$$

can be expressed by an equation for mass M in the same manner.

[Equation 4]

$$\frac{I_2}{I_1} = a_1M + b_1$$

$$\frac{I_3}{I_2} = a_2M + b_2$$

$$\frac{I_4}{I_3} = \frac{a_3M^2 + b_3M}{M + c_3}$$

The product of ratios of peak intensities can also be shown in Equation 5, when it is indicated as an equation associated with the mass M of an isotopic cluster. The products of the remaining $k^{th}$ peak intensities, $$\frac{I_{k-1}I_{k+1}}{I_k^2},$$

are calculated in the same manner. Herein, $t_1$, $t_2$, $t_3$, . . . are constants having values of ½, ⅔, ¾, . . . .

[Equation 5]

$$\frac{I_1I_3}{I_2^2} = t_1 + \frac{a_1}{M}$$

$$\frac{I_2I_4}{I_3^2} = t_2 + \frac{a_2M - b_2}{M^2 + c_2M + d_2}$$

$$\frac{I_3I_5}{I_4^2} = t_3 + \frac{a_3M^3 + b_3M + c_3}{M^4 + d_3M^3 + e_3M^2}$$

In the third step, the constants of the characteristic functions, $t(t_1, t_2, \ldots)$, $a(a_1, a_2, \ldots)$, $b(b_2, b_3, \ldots)$, $c(c_3, \ldots)$, $d(d_3, \ldots)$, $e(e_3, \ldots)$, are determined on the basis of given polypeptide data sampled from a database storing polypeptide data based on the shape of the previously known theoretical polypeptide spectra. Because the size of the polypeptide database is very large, the constants of the maximum, minimum and average functions of the above characteristic functions are calculated by uniformly sampling polypeptide data in each mass section and calculating the simulated spectrum of the isotopic cluster so as to approximate the polypeptide data. The maximum, minimum and average of the functions of the $k^{th}$ ratios of peptides having mass M, obtained through the above sampling and spectral calculation, are defined as $R_{max}(k, M)$, $R_{min}(k, M)$ and $R_{avg}(k, M)$, respectively, and the maximum, minimum and average of functions of the products of ratios are defined as $RP_{min}(k, M)$, $RP_{max}(k, M)$ and $RP_{avg}(k, M)$, respectively.

FIG. 1 shows examples of maximum, minimum and average functions for $I_2/I_1$. As can be seen in FIG. 1, each of the maximum $R_{max}(k, M)$, minimum $R_{min}(k, M)$ and average $R_{avg}(k, M)$ of the ratio functions increase according to a constant slope with an increase in the mass.

Figure 2:
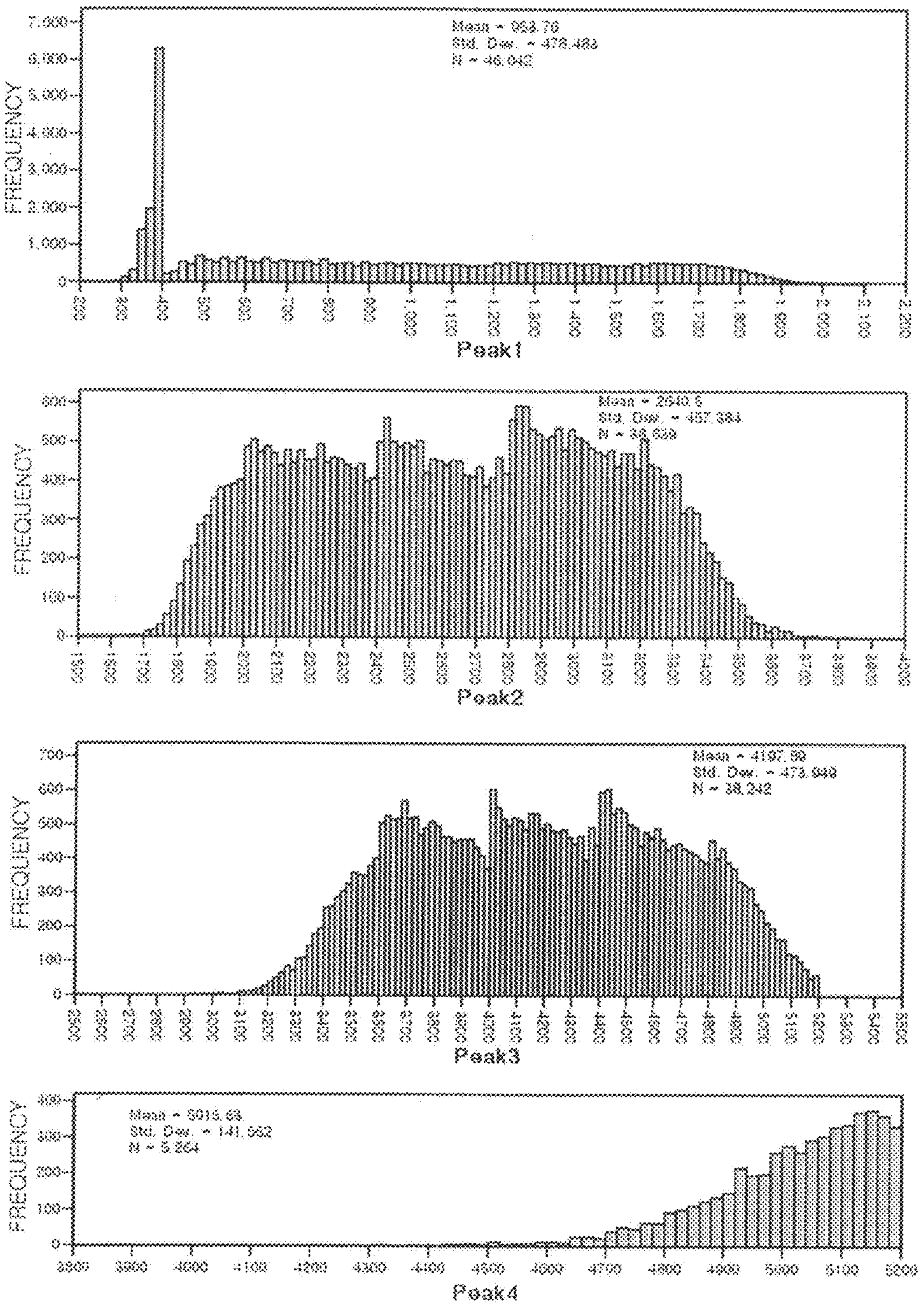
FIG. 2 shows the range of distribution of mass around the location of a peak, having the highest peak, in simulated spectral data according to an embodiment of the present invention.

Additionally, through simulated spectral data, the location of the strongest peak in an isotopic cluster can be seen. FIG. 2 shows an example of a mass distribution range around the location of the strongest peak in the simulated spectral data. Thus, the subsequent calculation of scores can be performed with reference to the location of the strongest peak in the mass range. For example, in the case of masses of less than 2000 Da, the first peak Peak 1 is the strongest, and other peaks (Peaks 2, 3 and 4) are small, and the when the ratio $I_2/I_1$ is suitable, the first peak Peak1 is assigned great weight.

Mode for Invention

Algorithm for Determining Isotopic Cluster and Monoisotopes

Figure 3:
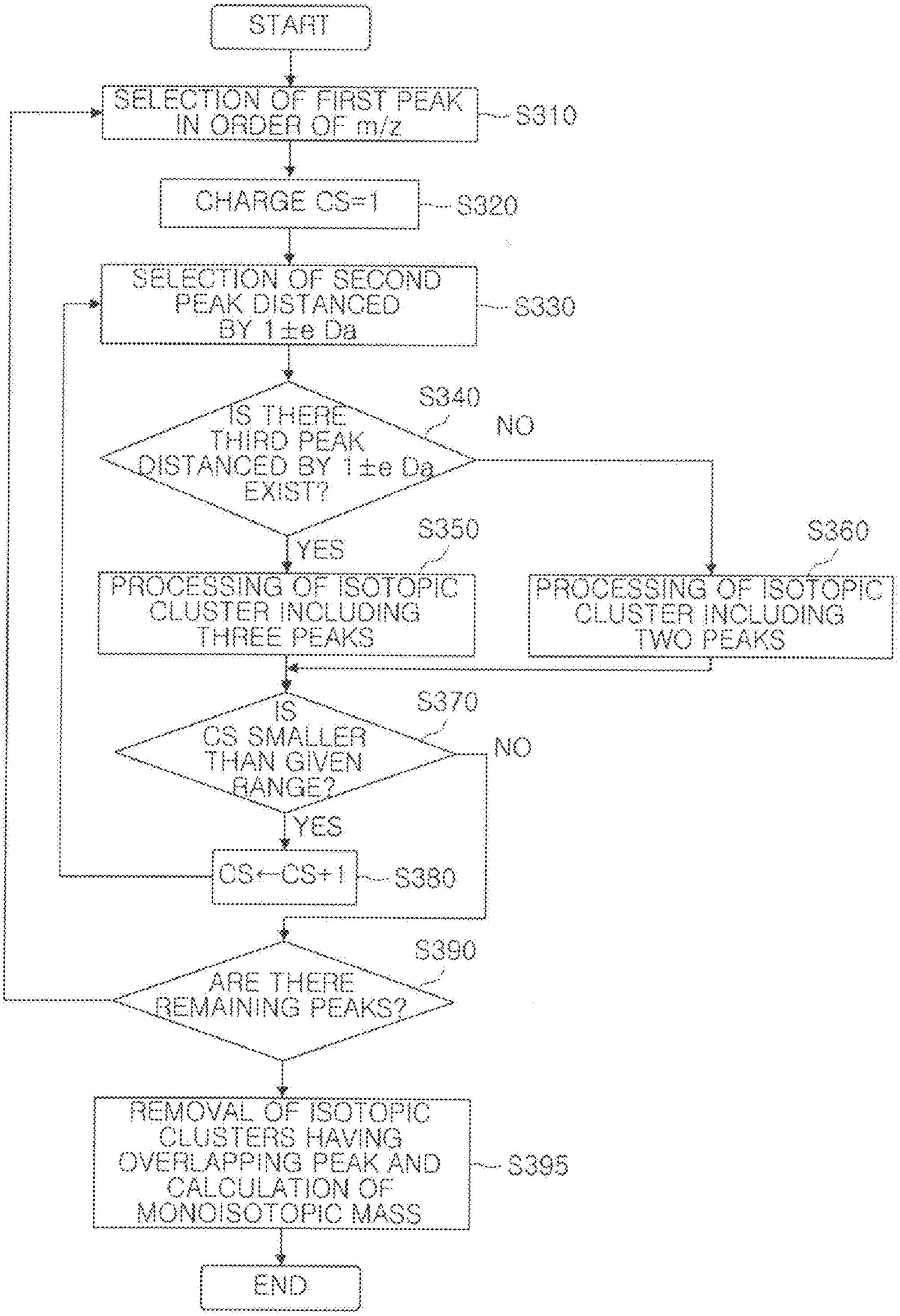
FIG. 3 is a flowchart explaining an algorithm of determining monoisotopic clusters and monoisotopes according to an embodiment of the present invention.

An algorithm for determining an isotopic cluster and a monoisotope will now be described. The entire algorithm, based on the above-described probabilistic model, is shown in FIG. 3. In the overall algorithm, each of the peaks in mass spectra is selected in the order of mass-to-charge ratio (m/z), and an isotopic cluster consisting of possible peaks 1 Da away from the relevant peak is found. That is, the first peak is selected in the order of m/z (S310), and a charge state CS is defined as 1 (S320). When the second and third peaks 1 Da away from the first peak are found, an error range e of about 10 ppm is set in the vicinity 1 Da away from the first peak, and all peaks in the relevant region apart (1±e) Da from the first peak are considered (S340).

As described above, up to three peaks having a distance of 1 Da from the selected peak are examined, the relevant isotopic cluster is determined, and the number of cases is divided, according to the peak number of the relevant isotopic cluster, into two. If the number of peaks in the relevant isotopic cluster is three, the ratios of the peaks and the product of the ratios are all applied to calculate the score of the isotopic cluster (S350), and on the other hand, if the number of peaks is two, only the ratio of peaks is applied to calculate the score of the isotopic cluster (S360). This procedure is repeated in consideration of all charge quantities in the predetermined range of about (1-10) z (S370 and S380).

In the case where the number of peaks in the relevant isotopic cluster is three, whether additional peaks with a distance of 1 Da exist after the isotopic cluster can be examined, after the score of the isotopic cluster is calculated (S390). Isotopic clusters having high scores in given mass spectra in the charge state CS range of (1-10) z are determined in the above-described procedures, and then, if these isotopic clusters include common overlapping peaks, the remaining overlapping clusters are removed, while only the best cluster among them remains. Then, the accurate monoisotopic mass of each of the isotopic clusters is determined (S395).

Figure 4:
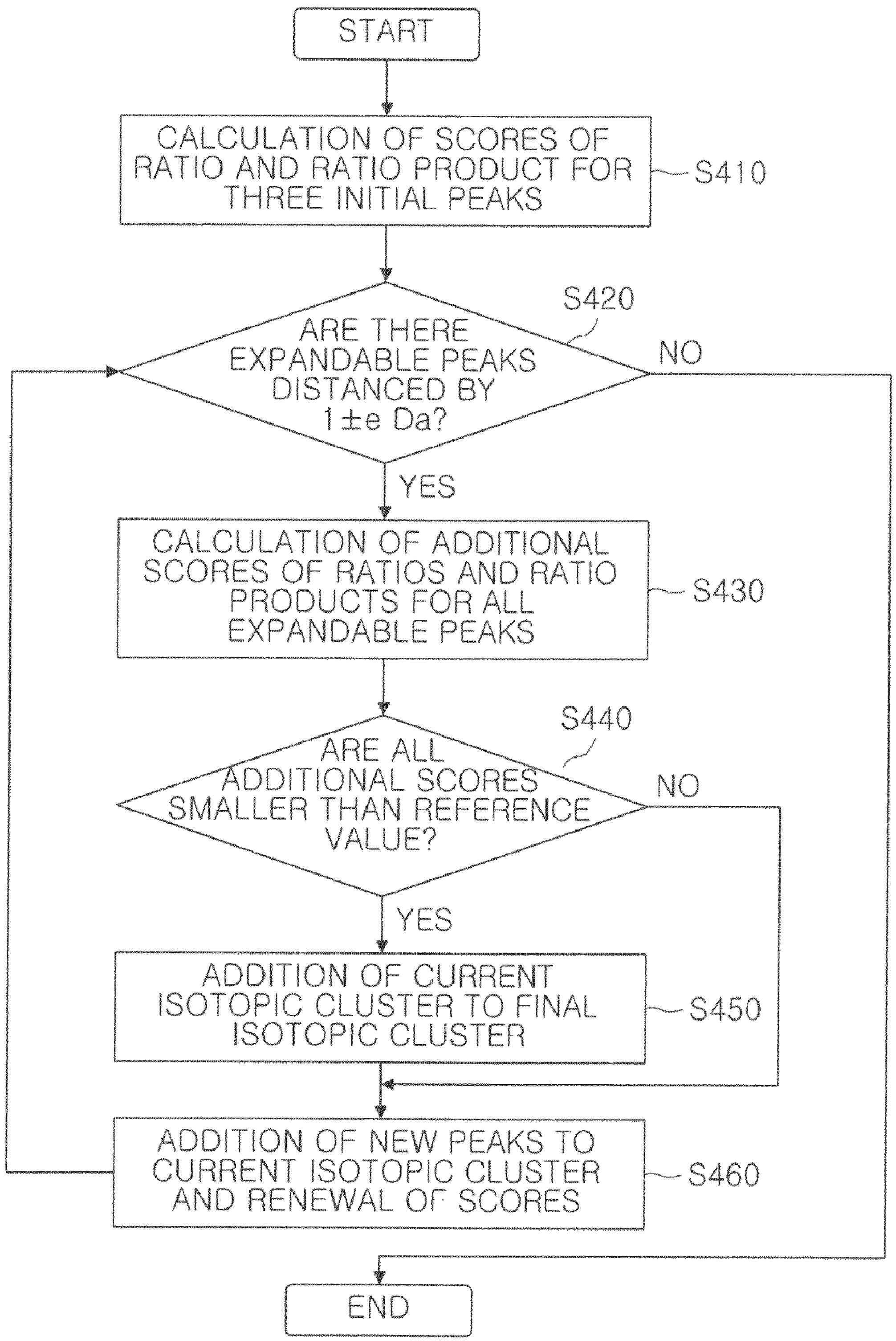
FIG. 4 is a flowchart explaining a method for processing an isotopic cluster including more than three peaks according to an embodiment of the present invention.

The detailed steps of the case in which the isotopic clusters including three or more peaks are processed are as shown in FIG. 4. First, the score of an initial isotopic cluster having three peaks is calculated using ratio and ratio product (S410). Using the monoisotopic mass M expected in the isotopic cluster, the ratio of peaks in the isotopic cluster is scored for the similarity to the range of the pre-determined ratio characteristic functions, $R_{min}(k, M)$, $R_{max}(k, M)$ and $R_{avg}(k, M)$. If there is a missing peak before the isotopic cluster, whether the intensity of peaks around that peak in the spectrum is actually smaller than other peaks is reflected in the calculation of the score.

As the initial isotopic cluster is determined, peaks with a distance of 1 Da in the back portion are found, the peaks are added to the isotopic cluster, and the score is renewed. Specifically, when expandable peaks with a distance of 1 Da are found, an error range e of about 10 ppm is set in the vicinity with a distance of 1 Da, and all expandable peaks in the relevant region at distance of (1±e) Da are considered (S420). If one or more expandable peaks exist, the ratio and ratio product for each peak are applied to calculate the additional score of the relevant isotopic cluster (S430). Herein, if each of the additional scores is less than a threshold score, the current isotopic cluster is added to the final isotopic cluster (S440 and S450). Herein, a missing peak can also exist after the final peak of the isotopic cluster, and whether peaks around that peak in the spectrum can actually disappear due to their low intensities is taken into account in the calculation of the score. Then, regardless of whether it is added to the final isotopic cluster, each of the expandable peaks is added to the current isotopic cluster to make a new isotopic cluster and renew the score (S460). New isotopic clusters corresponding in number to the number of expandable peaks are made. For each of the newly made isotopic clusters, the above procedures are repeated until there is no expandable peak.

In the above procedure, the calculation of the score of the isotopic cluster having three peaks is performed as follows. For example, the score according to the three peaks is calculated as the sum of the score of each of two ratios $I_{k+1}/I_k$ and $I_{k+2}/I_{k+1}$ and the ratio product of $I_k \cdot I_{k+2}/I_{k+1}^2$, when the first peak in the found isotopic cluster is assumed to be the k$^{th}$ peak of the theoretical isotopic cluster. Herein, for isotopic clusters having a score higher than a threshold score, the score added when the 1$^{st}$ peak is expanded is the sum of the score of ratio $I_l/I_l/I_{l-1}$ and the score of the ratio product $I_{l-2} \cdot I_l/I_{l-1}^2$. k is attempted in all cases for values ranging from 1 to 3.

In other words, when three peaks falling in the isotopic cluster are found, the peaks are assumed to be the k$^{th}$ peak to the k+2$^{nd}$ peak in the theoretical isotopic cluster, and the score of each of two ratios, calculated from the three peaks, the product of the ratio, are summed. Also, the results of correction of peaks before the isotopic cluster are reflected in the score of the relevant isotopic cluster. Moreover, if expandable peaks additionally exist in the isotopic cluster having a score higher than the threshold score, the score of one ratio and the score of one ratio product for each of the peaks are summed, and after the completion of expansion, correction for peaks after the isotopic cluster is reflected in the score of the relevant isotopic cluster.

The detailed steps of the case in which an isotopic cluster including two peaks is processed comprise two steps, that is, the score of the ratio of two peaks, $I_{k+1}/I_k$, which falls in the range of $R_{min}$ and $R_{max}$ and is close to $R_{avg}$, and the correction of missing peaks in the front and back of the isotopic cluster. In the two steps, in the same manner as in the case in which the isotopic cluster including three or more peaks is processed, the score of the ratio and the score of the ratio product are summed up, and the correction value therefor is calculated. In other words, if the number of peaks found in the isotopic cluster is two, the score of one ratio according to the two peaks is calculated, and the correction of peaks in the front and back of the isotopic cluster is reflected in the score of the relevant isotopic cluster.

Method of Calculating Score Using Ratio and Ratio Product

Hereinafter, a method of calculating a score using ratio and a ratio product will be described in further detail. When an isotopic cluster is found in an algorithm, a score is calculated using the ratio of peaks or one ratio product obtained from three peaks. In this section, this scoring method will be explained.

The method of calculating a score using a ratio is as follows. In a polypeptide having mass M, the score (S) of the ratio (X) between the k$^{th}$ peak and the k+1$^{st}$ peak is defined according to Equation 6 using the maximum value $R_{max}(k, M)$, the average value $R_{avg}(k, M)$ and the minimum value $R_{min}(k, M)$ of the k$^{th}$ ratio according to mass M.

$$S = \begin{cases} \frac{R_{max}(k, M) - X}{R_{max}(k, M) - R_{avg}(k, M)} & \text{if } X > R_{avg}(k, M) \\ \frac{X - R_{min}(k, M)}{R_{avg}(k, M) - R_{min}(k, M)} & \text{if } X \le R_{avg}(k, M) \end{cases} \quad \text{[Equation 6]}$$

When the score is defined as described above, it will be a positive number when the ratio is between the maximum and the minimum, and will otherwise be a negative number. The closer the score is to the average, the more similar it is to the spectral shape of the theoretical isotopic cluster, and thus it increases, having a maximum value of 1. For the maximum, minimum and average of ratio according to mass, the functions, obtained through sampling from the database in the pretreatment step and considering errors, are used. The calculation of a score using the ratio product can also be performed according to an equation similar to Equation 6, for calculating the score using the ratio.

The method of calculating the score can also be performed according to the following method using probability distribution. Because the ratio around mass M is in accordance with a regular distribution, the score S is calculated using the following function $S_N$, which is based on an average $R_{avg}(k, M)$ and a standard deviation $R_{dev}(k, M)$.

$$S = S_N\left(\frac{X - R_{avg}(k, M)}{R_{dev}(k, M)}\right) \quad \text{[Equation 7]}$$

If the amount of data around mass M is sufficiently large, $I_{k+1}/I_k$ is in accordance with a regular distribution. The characteristic function of a ratio is approximated as a linear function of mass, aM+b, and mass is a linear combination of the number $n_X$ of atoms and mass $w_X$, that is, $M=\Sigma w_X n_X$. Thus, if the number of atoms in a polypeptide is in accordance to a regular distribution, $I_{k+1}/I_k$ is also in accordance with the regular distribution. S can be calculated by calculating the distribution of ratio in each mass region using simulated spectral data and calculating the standard deviation function $R_{dev}(k, M)$ therefrom. The calculation of scores using the ratio product can also be performed according to an equation similar to Equation 7, supposing a regular distribution or a probability distribution modified therefrom.

Method of Maximum and Minimum Values of Ratio and Ratio Product in Consideration of Errors of Peaks Hereinafter, a method of the maximum and minimum values of ratio and ratio product in consideration of the errors of peaks will be described. In the found peak data, the peak intensity values do not accurately coincide with the theoretical values. Thus, the ratio and ratio product calculated from the found peak data frequently deviate from the range of the maximum and minimum values obtained through sampling from the database in the pretreatment step. Thus, for the maximum and minimum values, which are used to calculate scores using ratio and ratio product, functions obtained through sampling in the pretreatment step are used after expansion in consideration of errors.

In the maximum value ($R_{max}$) and minimum value ($R_{min}$), obtained through sampling, values ($R'_{max}$ and $R'_{min}$), which take into account errors (e), can be defined according to Equation 8:

$$R'_{max} = \begin{cases} R_{max}/(1-e) & \text{if } R_{max} > 1 \\ R_{max} \times (1+e) & \text{if } R_{max} \le 1, \end{cases} \quad \text{[Equation 8]}$$

$$R'_{min} = \begin{cases} R_{min}/(1+e) & \text{if } R_{min} > 1 \\ R_{min} \times (1-e) & \text{if } R_{min} \le 1, \end{cases}$$

$$(0 \le e \le 1)$$

This method is based on the assumption that errors are likely to occur in peaks having low intensity. That is, in order to determine the peak having the lower peak among two peaks so as to consider the case in which the intensity of the peak is increased or decreased by errors, the maximum and minimum functions are expanded as shown in Equation 8 and are used to score the isotopic cluster.

In the ratio product, the peak having the lowest intensity is always included in the molecule of the equation, and thus the equation is easily determined.

In the maximum value ($RP_{max}$) and the minimum value ($RP_{min}$) of the ratio product obtained through sampling, the values ($RP'_{max}$ and $RP'_{min}$) taking errors (e) into account can be defined according to equation 9.

$$RP'_{max}=RP_{max}\times(1+e),$$

$$RP'_{min}=RP_{min}\times(1-e) \quad \text{[Equation 9]}$$

Method for Correction of Missing Peaks Before and After Isotopic Cluster

Hereinafter, the method for the correction of missing peaks before and after the isotopic cluster will be described. When the score of the isotopic cluster is found in the algorithm, if there are missing peaks in the front and back of the isotopic cluster, the correction of scores for the peaks is performed.

If there are missing peaks in the front of the isotopic cluster, the first peak included in the found isotopic cluster is not the first peak in the theoretical isotopic cluster of the relevant polypeptide. When the first peak in the found isotopic cluster is assumed to be the $k^{th}$ peak in the theoretical isotopic cluster, the theoretical minimum of intensity of the $k-1^{st}$ peak, $I_{k-1,min}$, can be defined as $I_{k-1,min}=I_k/R_{max}(k-1,M)$ from the intensity of the $k^{th}$ peak, $I_k$, and the maximum function of the ratio, $R_{max}(k, M)$. Thus, the peak having the strongest intensity is found in the total mass spectrum in a given range in which the $k-1^{st}$ peak can exist in the entire mass spectrum, for example, before 1 Da. Then, only when the intensity is smaller than $I_{k-1,min}$, the peak is assumed to be the $k-1^{st}$, and the score of the ratio to the $k^{th}$ peak, $(I_k/I_{k-1})$, is calculated to thus reduce the score of the isotopic cluster.

The correction for missing peaks in the back of the isotopic cluster is also performed using a method similar to the above method. When the final peak in the found isotopic cluster is assumed to be the $k^{th}$ peak in the theoretical isotopic cluster, the theoretical minimum of the $(k+1)^{st}$ peak, can be defined as $I_{k+1,min}=I_k \times R_{min}(k, M)$ from the intensity of the $k^{th}$ peak, $I_k$, and the minimum of ratio, $R_{min}(k, M)$. Thus, the peak having the greatest intensity is found in a given range in the total mass spectrum, in which the $(k+1)^{st}$ peak can be present, for example, after 1 Da. Then, only when the intensity is lower than $I_{k+1,min}$, the peak is assumed to be the $k+1^{st}$ peak, and the score of the ratio to the $k^{th}$ peak, $(I_k/I_{k+1})$, is calculated to reduce the score of the isotopic cluster.

Method of Applying Score Weight According to Mass

Figure 5:
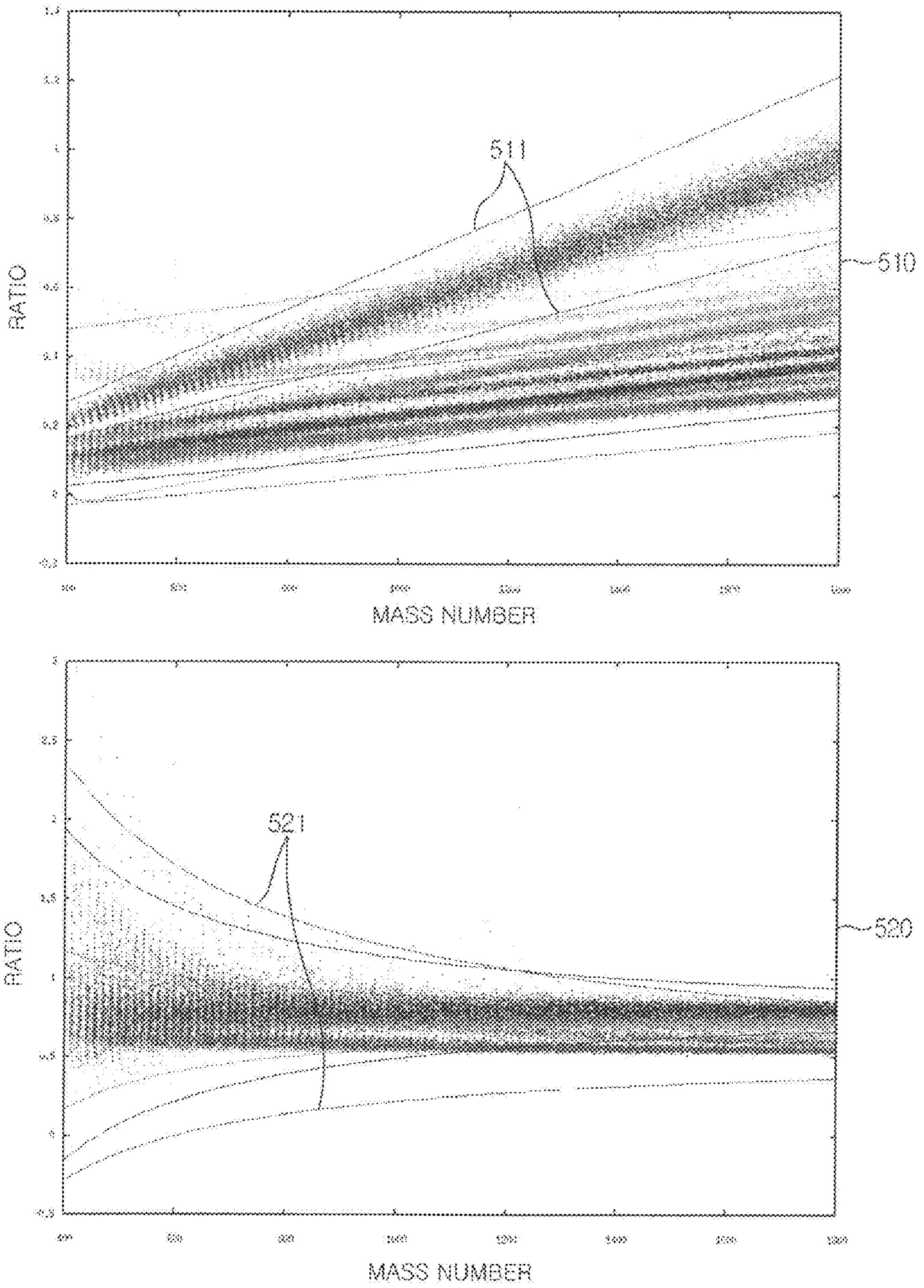
FIG. 5 shows the distribution of peak ratio and the distribution of ratio product as a function of mass according to an embodiment of the present invention.

Hereinafter, a method of applying score weight according to mass will be described. In order to obtain better results, the above-described method of calculating scores is modified to apply score weight according to mass. In FIG. 5, reference number 510 indicates the distribution of ratios below a mass of 1800, and reference 520 indicates the distribution of ratio products below a mass ratio of 1800. As shown in FIG. 5, if the mass is low, the range of distribution of ratios in curves of $I_3/I_2$, $I_4/I_3$, $I_5/I_4$, etc., except for the maximum and minimum curves 511 of $I_2/I_1$, is wider than the average value, and the ratios tend to overlap each other. Also, the range of distribution of ratio products is wide in all curves, including the maximum and minimum curves 521 of $(I_1I_3/I_2^2)$, and the product ratios overlap each other, similar to the distribution of ratios. Thus, this is of little help in determining mass. In the above example, the point at which the intensity of the first peak and the intensity of the second peak are theoretically equal to each other is a mass of about 1800, and thus it can be assumed that the first peak always appears below a mass of 1800. Accordingly, below a mass of 1800, two-fold weight is applied to the most reliable ratio score of $I_2/I_1$, and the score of ratio can be calculated without calculating the score of ratio product.

Method of Removing Isotopic Clusters Having Overlapping Peak

A method of removing isotopic clusters having an overlapping peak will now be described. When isotopic clusters are found according to the above-described algorithm, one peak can be included in several isotopic clusters. For this reason, after the completion of the finding, if isotopic clusters including the same peak exist among the found isotopic clusters having scores higher than a threshold score, an operation of removing the isotopic clusters having the same peak while leaving only one isotopic cluster, having a high priority, is performed.

Figure 6:
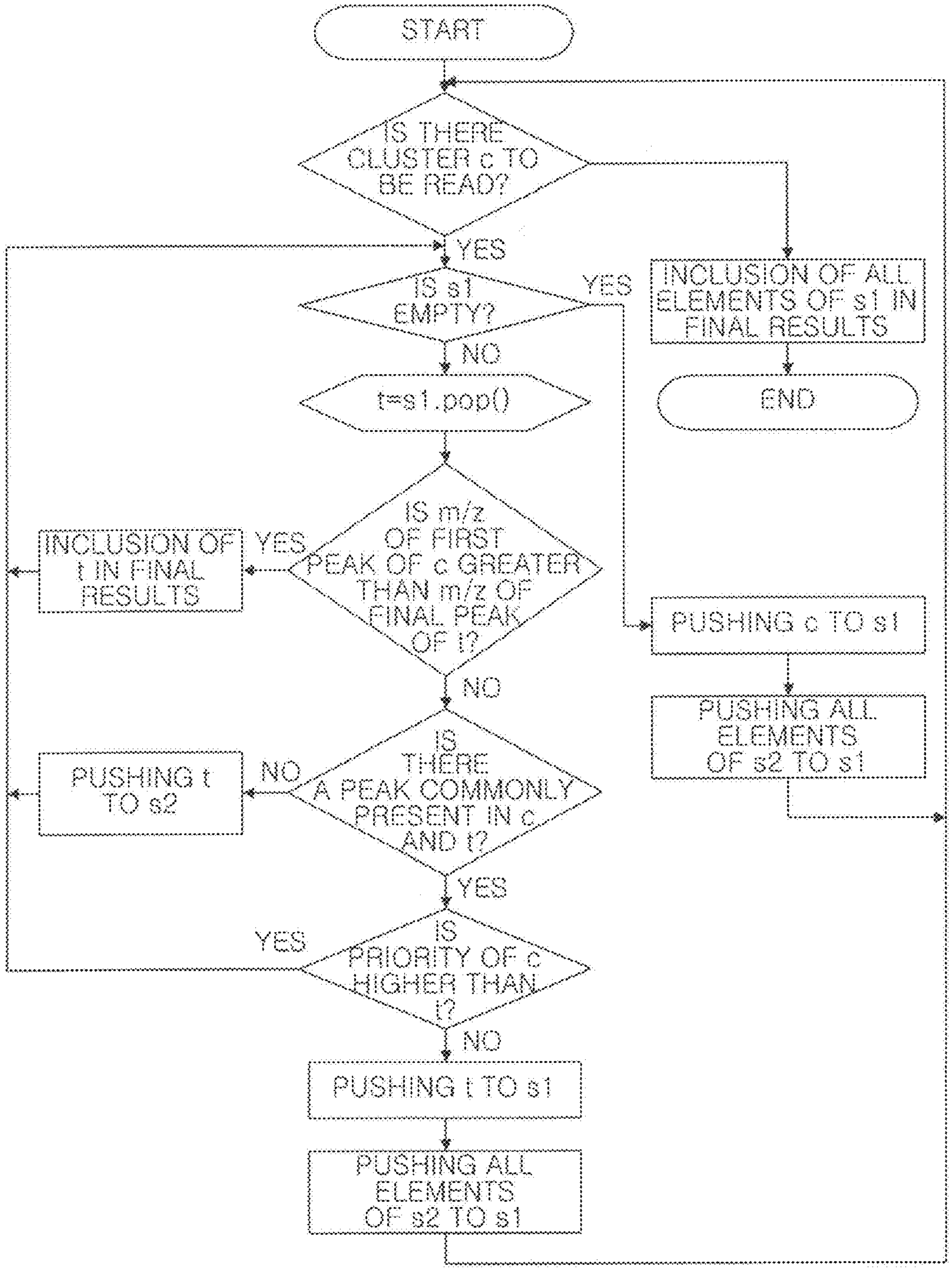
FIG. 6 is a flowchart explaining a method of removing isotopic clusters having an overlapping peak according to an embodiment of the present invention.

The isotopic clusters obtained after the completion of the finding are arranged in the order of the m/z value of the first peak included in the isotopic clusters. The isotopic clusters read in regular sequence, and the removal of overlapping isotopic clusters is performed through the procedure shown in FIG. 6. Herein, two stacks, $s_1$ and $s_2$, which use the isotopic clusters as elements, are used. At the end of each step, among the isotopic clusters which have been previously read, isotopic clusters, which have no common overlapping peak and in which the m/z value of the final peak is larger than the m/z value of the first peak of the isotopic cluster c, which has now been read, are stored in the stack $s_1$. The stack $s_2$ is a temporary stack for processing in each step, and temporary isotopic clusters, which have no common peak overlapping with the lately read isotopic cluster c and in which the m/z value of the final peak is larger than the m/z value of the first peak, are stored in the stack $s_2$.

The priority of two isotopic clusters is determined through the following procedure. First, among peaks included in the isotopic clusters, peaks having the highest intensity are compared, and the isotopic cluster including the peak having the higher intensity has higher priority. When the peak intensities are the same, the isotopic cluster having the larger charge state has higher priority. When the charge quantities are also the same, the isotopic cluster having the higher isotopic cluster score has higher priority.

Method of Calculating Monoisotopic Mass of Monoisotope

A method of calculating the monoisotopic mass of a monoisotope will now be described. In the present invention, for the accurate calculation of monoisotopic mass, a weight is applied to each peak such that highly reliable mass values can be calculated from peaks belonging to isotopic clusters having scores higher than the threshold score. The mass of each of peaks in isotopic clusters is converted from the mass-to-charge ratio (m/z) of the isotopic clusters, and when the mass obtained from the first peak is subtracted from the mass of each peak, the monoisotopic mass of each peak can be calculated.

The final monoisotopic mass of isotopic clusters is calculated as the weighted average of monoisotopic masses calculated from the respective peaks, and the first, second and third peaks are given weights $w_1$, $w_2$ and $w_3$, respectively. Herein, the weight is determined in consideration of two factors, peak intensity and the accuracy of the corrected mass spectrum. If the mass is small, then the intensity of the first peak is high and no error is introduced during mass correction, leading to high reliability, and thus a great weight is given. If the mass is large, the intensities of peaks are increased, and thus the reliability of the peak having the highest intensity is high, but errors can be introduced during mass correction, except for the first peak. For this reason, a relatively low weight is given. In the present invention, each of the weights is determined in consideration of both the intensity of peaks and the error of mass correction.

Because the difference in mass between isotopes varies depending on the kind of element, the composition of a polypeptide and the ratio of the existence of isotopes should be considered in calculating the average mass differences $1_{avg}$, $2_{avg}$, $3_{avg}$, . . . between the first peak and the $k^{th}$ peaks. Because the actual composition of the peptide cannot be known, it can be expressed as an equation for mass M, as shown in Equation 10 using the averagine composition.

[Equation 10]

$$1_{avg} = \frac{1}{Y}\left(1_C n_C \frac{P(C,1)}{P(C,0)} + 1_H n_H \frac{P(H,1)}{P(H,0)} + 1_N n_N \frac{P(N,1)}{P(N,0)} + 1_O n_O \frac{P(O,1)}{P(O,0)} + 1_S n_S \frac{P(S,1)}{P(S,0)}\right)$$

$$2_{avg} = \frac{1}{Y^2/2+Z}\left(\begin{array}{c} 1_C n_C^2 \frac{P(C,1)^2}{P(C,0)^2} + 1_H n_H^2 \frac{P(H,1)^2}{P(H,0)^2} + \ldots\ 1_S n_S^2 \frac{P(S,1)^2}{P(S,0)^2} + \\ (1_C 1_H) n_C n_H \frac{P(C,1)P(H,1)}{P(C,0)P(H,0)} \ \ldots + (1_O 1_S) n_O n_S \frac{P(O,1)P(S,1)}{P(O,0)P(S,0)} + \end{array}\right)$$

$$\cong \frac{a_2 + b_2/M}{c_2 + d_2/M}$$

$$3_{avg} = \frac{1}{Y^3/6+YZ}(\ \ldots\ ) \cong \frac{a_3 + b_3/M}{c_3 + d_3/M}$$

In Equation 10, $a_2$, $b_2$, . . . $d_3$ are constants which can be calculated from the mass and probability of existence of isotopes, and $4_{avg}$, $5_{avg}$, . . . can also be calculated in the same manner. In this example, the difference $1_{avg}$ in mass between the first peak and the second peak can be calculated from a constant of 1.002858, and the difference $2_{avg}$ in mass between the first peak and the third peak can be calculated as an approximate value using the approximate mass of the first peak as M. The theoretical values resulting from this algorithm can be used as comparative data for how they differ from values resulting from monoisotopes found according to the present invention.

Functions used in the method disclosed herein can be embodied as computer-readable codes in computer-readable recording media. The computer-readable recording media include all kinds of recording systems in which computer-readable data are stored. Examples of the computer-readable recording media include ROM, RAM, CD-ROM, magnetic tapes, floppy disks, optical data storage units and the like, and in addition, those embodied in the form of carrier waves (for example, transmission over the Internet). Also, the computer-readable recording media can be dispersed in computer systems connected by networks, such that computer-readable codes can be stored and executed in a distributed manner. Optimal embodiments have been disclosed in the drawings and in this specification. Here, particular terms have been used simply to explain the present invention, not to restrict meanings or limit the scope of the present invention claimed in the following claims. Accordingly, those skilled in the art will appreciate that various modifications, additions and substitutions are possible, without departing from the scope and spirit of the invention as disclosed in the accompanying claims.

INDUSTRIAL APPLICABILITY

The method of determining a monoisotopic cluster to the mass of monoisotopes according to the present invention is very useful in the method and system for conducting mass spectrometry on a peptide mixture.

The invention claimed is:

1. A non-transitory computer readable medium having computer executable code stored thereon which, when executed, causes a computer to perform a method comprising:

determining a probabilistic model of an isotopic cluster;

finding isotopic clusters from mass spectra; and determining monoisotopic masses of the isotopic clusters, using the probabilistic model, wherein the step of determining the probabilistic model of an isotopic cluster comprises:

approximating an intensity ($I_k$);

determining an intensity of a $k^{th}$ peak in the isotopic cluster ($I_k$), a ratio ($I_{k+1}/I_k$) of two peak intensities, and a ratio product $$\left(\frac{I_{k-1}I_{k+1}}{I_k^2}\right)$$

of two ratios obtained from three peaks, using probabilistic equations; and determining maximum, minimum and average functions ($R_{max}$(k, M), $R_{min}$(k, M) and $R_{avg}$(k, M)) for the $k^{th}$ ratio of a polypeptide having a mass of M, and maximum, minimum and average functions ($RP_{max}$(k, M), $RP_{min}$(k, M) and $RP_{avg}$(k, M)) for the ratio product of the $k^{th}$ ratio of the polypeptide having the mass of M, wherein $I_{k+1}$ is an intensity of a peak with a mass 1 Da larger than $I_k$, and $I_{k-1}$ is an intensity of a peak with a mass 1 Da smaller than $I_k$.

2. The non-transitory computer readable medium of claim 1, wherein the intensity ($I_k$) is expressed as an equation based on a number of elements in the polypeptide and a probability of existence of an isotope of each of the elements, and the probabilistic equations of the ratio and ratio product, calculated from the equation for the intensity , are expressed as functions including the mass M.

3. The non-transitory computer readable medium method of claim 1, wherein the step of determining the maximum, minimum and average functions of the ratio and the ratio product comprises sampling polypeptide data from a database, calculating a simulated spectrum so as to approximate the polypeptide data, and determining constants of the maximum, minimum and average functions of the ratio and the ratio product.

4. The non-transitory computer readable medium of claim 1, wherein the step of finding the isotopic clusters from the mass spectra and determining the monoisotopic masses of the isotopic clusters comprises:

selecting peaks in the order of mass-to-charge ratio (m/z) in a mass spectrum, and then finding isotopic clusters, having a charge state of 1-10 z, starting from the peaks;

dividing the found isotopic clusters into cases comprising more than 3 peaks and cases consisting of two peaks, and calculating a score of each of the cases;

removing any one of two isotopic clusters having an overlapping peak, from the isotopic clusters having scores higher than a threshold score; and calculating the monoisotopic mass of each of the isotopic clusters having the scores higher than the threshold score.

5. The non-transitory computer readable medium of claim 4, wherein, in the step of calculating the score, if three peaks belonging to the isotopic cluster are found, they are assumed to be a $k^{th}$ peak, a $k+1^{st}$ peak and a $k+2^{nd}$ peak in a theoretical isotopic cluster, the score for each of the two ratios and a score for one the ratio product calculated from the three peaks are summed, and a correction of peaks before the isotopic cluster is reflected in the score of the isotopic cluster, and if expandable peaks additionally exist in isotopic clusters having scores higher than the threshold score, the score for the ratio and the score for the ratio product for each peak are summed and added to the score of isotopic cluster, and after completion of expansion, correction of peaks after the isotopic cluster is reflected in the score of the relevant isotopic cluster.

6. The non-transitory computer readable medium of claim 5, wherein the maximum, minimum and average functions for the ratio and the ratio product, obtained through sampling from the probabilistic model, are used to determine scores for the ratio and the ratio product, such that the scores increase as the ratio and the ratio product approach average, the scores are positive in a range between a maximum and a minimum, and the scores are negative when they deviate from the range between the maximum and the minimum.

7. The non-transitory computer readable medium of claim 6, wherein the maximum and minimum functions, obtained through sampling, are expanded in consideration of a case in which a peak having a lower intensity among two peaks used in calculation of the ratio increases or decreases by an error, and the expanded maximum and minimum functions are used in calculation of the score.

8. The non-transitory computer readable medium of claim 5, wherein, in the correction for the peaks before the isotopic cluster, if the first peak of the isotopic cluster is not a first peak in a theoretical isotopic cluster, a largest peak is found in a whole mass spectrum in a given range in which the peaks before the isotopic cluster exist, and if the intensity of the largest peak is smaller than a theoretical minimum value, a score for the ratio of the first peak to the largest peak is calculated and subtracted from the score of the isotopic cluster; and, in the correction for the peaks present after the isotopic cluster, a largest peak is found in the whole mass spectrum in a given range in which the peaks after the isotopic cluster exist, if the intensity of the largest peak is smaller than a theoretical minimum value, a score for the ratio of the final peak to the largest peak is calculated and subtracted from the score of the isotopic cluster.

9. The non-transitory computer readable medium of claim 5, wherein the average deviation function for each of the ratio and ratio product obtained through sampling from the probabilistic model, and a standard deviation function for each of the ratio and ratio product calculated from a simulated spectral data, are used to determine scores for the ratio and the ratio product, assuming that the probability distribution of ratio and ratio product for a specific mass is a regular distribution.

10. The non-transitory computer readable medium of claim 4, wherein, in the step of calculating the score, if only two peaks belonging to the isotopic cluster are found, the score for the ratio according to the two peaks is calculated, and correction for peaks before and after the isotopic cluster is reflected in the score of the isotopic cluster.

11. The non-transitory computer readable medium of claim 10, wherein the maximum, minimum and average functions for the ratio and ratio product, obtained through sampling from the probabilistic model, are used to determine scores for the ratio and the ratio product, such that the scores increase as the ratio and the ratio product approach average, the scores are positive in a range between a maximum and a minimum, and the scores are negative when they deviate from the range between the maximum and the minimum.

12. The non-transitory computer readable medium of claim 11, wherein the maximum and minimum functions, obtained through sampling, are expanded in consideration of a case in which a peak having a lower intensity among two peaks used in calculation of the ratio increases or decreases by an error, and the expanded maximum and minimum functions are used in calculation of the score.

13. The non-transitory computer readable medium of claim 10, wherein the average function for each of the ratio and ratio product, obtained through sampling from the probabilistic model, and a standard deviation function for each of the ratio and ratio product calculated from a simulated spectral data, are used to determine scores for the ratio and the ratio product, assuming that the probability distribution of ratio and ratio product for a specific mass is a regular distribution.

14. The non-transitory computer readable medium of claim 10, wherein, in the correction for the peaks before the isotopic cluster, if the first peak of the isotopic cluster is not a first peak in a theoretical isotopic cluster, a largest peak is found in a whole mass spectrum in a given range in which the peaks before the isotopic cluster exist, and if the intensity of the largest peak is smaller than a theoretical minimum value, a score for the ratio of the first peak to the largest peak is calculated and subtracted from the score of the isotopic cluster; and, in the correction for the peaks present after the isotopic cluster, a largest peak is found in the whole mass spectrum in a given range in which the peaks after the isotopic cluster exist, if the intensity of the largest peak is smaller than a theoretical minimum value, a score for the ratio of the final peak to the largest peak is calculated and subtracted from the score of the isotopic cluster.

15. The non-transitory computer readable medium of claim 4, wherein, among all found isotopic clusters, only one isotopic cluster having a high priority in two isotopic clusters having a common overlapping peak remains.

16. The non-transitory computer readable medium of claim 15, wherein the priority is determined by comparison in the order of higher intensity of the peak, larger charge state of the peak, and higher score of the isotopic cluster.

17. The non-transitory computer readable medium of claim 4, wherein, in the step of calculating the monoisotopic mass, greatest weight is given to a peak having the highest intensity in the isotopic cluster.

* * * * *